United States Patent [19]

Rapoport et al.

[11] 4,054,566

[45] Oct. 18, 1977

[54] PROCESS FOR CONVERTING NEOPINONE TO CODEINONE

[75] Inventors: Henry Rapoport; Randy B. Barber, both of Berkeley, Calif.

[73] Assignee: The Regents of the University of California, Berkeley, Calif.

[21] Appl. No.: 665,602

[22] Filed: Mar. 10, 1976

[51] Int. Cl.$^2$ .................. C07D 489/00; C07D 489/02
[52] U.S. Cl. .................................................. 260/285
[58] Field of Search ......................................... 260/285

[56] References Cited

FOREIGN PATENT DOCUMENTS 593,832  3/1960  Canada

OTHER PUBLICATIONS

Rapoport et al., J. Am. Chem. Soc. 89(8), pp. 1942–1947 (1967).

Primary Examiner—Donald G. Daus
Assistant Examiner—Diana G. Rivers
Attorney, Agent, or Firm—R. J. Klostermann

[57] ABSTRACT

A process for converting neopinone alkaloid to codeinone alkaloid which involves treating neopinone with a hydrohalic acid in a suitable solvent under anhydrous conditions. It also relates to the compound 8-halodihydrocodeinone hydrohalide.

14 Claims, No Drawings

PROCESS FOR CONVERTING NEOPINONE TO CODEINONE

BACKGROUND OF THE INVENTION

The invention relates to a novel 8-halodihydrocodeinone hydrohalide and to a process for converting neopinone alkaloid or a mixture containing neopinone and codeinone alkaloids to essentially all codeinone.

DESCRIPTION OF THE PRIOR ART

Neopine is one of the alkaloids available from the opium poppy and it can readily be converted to neopinone. Likewise neopinone may be obtained from thebaine alkaloid according to the procedure described in our co-pending application entitled Metallic Derivatives of Neopinone Ketal, Serial No. 665,601, filed on the same date herewith. Since codeinone can be easily converted to codeine by reducing the ketone group of codeinone to a hydroxyl group, a procedure for converting neopinone to codeinone would be an advancement in the art.

BRIEF DESCRIPTION OF THE INVENTION

This invention relates to 8-halodihydrocodeinone hydrohalides represented by the following formula

FORMULA I

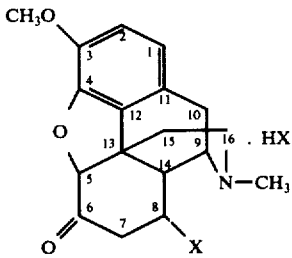

wherein X is a halogen.

These compounds are intermediates in the preparation of codeinone from neopinone or a mixture containing neopinone and codeinone.

Another aspect of this invention is directed to a process for preparing codeinone from neopinone or a mixture containing neopinone and codeinone which involves reacting neopinone or a mixture containing neopinone and codeinone with a hydrohalic acid under anhydrous conditions to convert neopinone or the mixture to the corresponding 8-halodihydrocodeinone hydrohalide and thereafter treating the 8-halodihydrocodeinone hydrohalide with a basic agent to form codeinone. The codeinone can be converted into codeine by the Gates method disclosed in U.S. Pat. No. 2,778,832 which is incorporated herein by reference.

As can readily be seen by having a process for converting neopinone or a mixture containing neopinone and codeinone to essentially all codeinone, another source of codeine is provided.

DETAILED DESCRIPTION OF THE INVENTION

As mentioned X represents a halogen. It is preferred that X be bromine or chlorine.

The novel compounds of this invention are prepared in the first step of the overall reaction for converting neopinone to codeinone in essentially quantitative yields. In the first step neopinone or a mixture containing neopinone and codeinone is reacted with a hydrohalic acid, preferably hydrogen chloride or hydrogen bromide under anhydrous conditions. Preferably, the reaction is effected in a suitable neutral non-protonic solvent. Examples of such solvents include chlorinated hydrocarbons, particularly low boiling point chloroalkanes such as methylene chloride, chloroform, carbon tetrachloride, 1,2-dichloroethane, and 1,1,3,3-tetrachloroethane, hydrocarbons, particularly aromatic carbons, such as benzene, ethers, particularly a di-lower alkyl ether such as diethyl ether diisopropyl ether and di-normal butyl ether, esters such as ethylacetate and β-ethoxy ethyl acetate, and cyclic ethers such as tetrahydrofuran, p-dioxane and tetrahydropyran.

While methylene chloride or chloroform for example may be successfully employed alone as the solvent, optimum yields are generally obtained utilizing solvents which are mixtures of solvents of the above class. Thus wherein ether is employed it is desirable to employ a solvent which is a mixture of the same with a chlorinated hydrocarbon, for example, chloroform and 1,2-dichloroethane.

The solvent may be used in quantities suitable for dissolving or suspending neopinone or the mixture containing neopinone and codeinone, for instance, in a weight ratio of solvent to neopinone or to the mixture of neopinone and codeinone of about 1:1 to about 500:1.

When a mixture containing neopinone and codeinone is employed it is generally a mixture containing any portion of codeinone from about 1% to about 99% by weight and from about 99% to about 1% neopinone by weight based on the total weight of the mixture. Typically, the mixtures contain about 1% to about 75% codeinone and from about 99% to about 25% neopinone. Of course, if the mixture is predominantly codeinone it would be necessary to use the process of the instant invention.

A sufficient amount of hydrohalic acid is employed in the practice of this invention to form the 8-halodihydroccodeinone hydrohalide which is typically from about 1.5 moles to about 5 moles per mole of neopinone and preferably, about 2 moles to about 4 moles. Although more than 5 moles can be employed this does not provide any significant advantage. Using less than 1.5 moles generally results in incomplete reaction.

The reaction is preferably carried out at a temperature in the range of from about −20° C. to about 50° C. A temperature of from about 0° C. to about 30° C. is preferred. Typically, the reaction is conducted under an inert and dry atmosphere, e.g. nitrogen. The reaction period ranges generally from a few minutes to a few hours, specifically from about 2 minutes to about 2 hours. In any specific case it is easy to determine the best period by a few preliminary experiments.

Of course, the reaction time may vary considerably according to the reaction conditions. In particular when anhydrous hydrochloric acid is used, the reaction time to obtain suitable results is generally about 30 minutes at room temperature. On the other hand when anhydrous hydrobromic acid is used the reaction time may be reduced to about 5 minutes at 0° C.

The sequence of addition of the neopinone to the hydrohalic acid is not critical. For example, the neopinone can be added to the hydrohalic acid or vice versa.

Regarding the second step of the process, it comprises treating the 8-halodihydrocodeinone hydrohalide with a basic agent in an aqueous medium, although this does not exclude treatment in an anhydrous medium. The purpose of the basic agent is to liberate the alkaloid. The basic agent may be a mild alkaline agent such as sodium bicarbonate or may be, for example, alkalimetal hydroxides, ammonia, alkaline earthmetal hydroxides and the corresponding carbonate and bicarbonate, salts having an alkaline action such as sodium acetate, trisodium phosphate and organic bases such as dimethyl amine or trimethyl amine.

A sufficient amount of the basic agent is employed to neutralize the 8-halodihydrocodeinone hydrohalide and thus liberate codeinone. Generally the amount of basic agent utilized should be such that the pH of the final mixture containing codeinone is from about 8 to about 13 at 0° C. to 25° C.

Isolation of the codeinone at the end of the reaction does not present any difficulty. It may be recrystallized if necessary from a suitable solvent. Alternatively, it may be recovered by extracting with a suitable water immiscible solvent such as chloroform and the like. As mentioned codeinone can then be converted to codeine by reducing the ketone group of codeinone to a hydroxyl group.

The invention will now be illustrated by the following examples:

EXAMPLE 1

Conversion of Neopinone to Codeinone

A solution of neopinone (100 mg., .336 mmol; 25% codeinone) in methylene chloride (.45 ml.); at 0° C. was treated with anhydrous HBr in ethyl ether (.45 ml.; 2.4 g. HBr/10 ml. ethyl ether) for 5 min. A ppt. formed immediately upon the addition of the HBr in ether. The reaction was quenched by partitioning between 0.2N NaOH and chloroform. The aqueous phase was extracted with several portions of chloroform. All of the chloroform extracts were combined, washed with water, dried over $Na_2SO_4$, filtered and evaporated in vacuo to give 95 mg. of codeinone (100% codeinone) as analyzed by nmr and reduction to codeine with sodium borohydride and analysis of the codeine by gc.

The above procedure was repeated using .45 ml. of HCl in ethyl ether (1.1 g, HCl/10 ml, ether) at room temperature for 30 min. instead of HBr/ethyl ether at 0° for 5 min.

The intermediate 8-halodihydrocodeinone-hydrohalides were isolated by evaporating the reaction and crystallization of the resulting solids from methanol.

NMR's for the bromo and chloro 8-halodihydrocodeinone-hydrohalides were similar each indicating the presence of two isomers in equivalent amounts, epimers at C-8 by two 3-O-$CH_3$ absorptions. The analysis for 8-chlorodihydrocodeinone-hydrochloride came out correct. These compounds were hygroscopic.

Anal. Calcd. for $C_{18}H_{21}NO_3Cl_2$: C, 58.38; H, 5.73; N, 3.78. Found: C, 58.3; H, 6.0; N, 3.7.

EXAMPLE 2

Conversion of Neopinone to Codeine

A solution of neopinone (0.943 g.; 3.17 mmol; from the previous example) in methylene chloride (1.4 ml.); was treated slowly (~1 min.) with HCl in ethyl ether (1.4 ml.; 1.1 g. HCl/10 ml.) while shaking and shaking was continued for 30 min. The solvents were then evaporated in vacuo from this mixture to give a yellow solid which was broken up and then shaken with 200 ml. $H_2O$ until dissolved. Chloroform (50 ml.) was added and then cooled to 0°. This mixture was then basified with aq. NaOH to pH 10 – 11 while cold and extracted with chloroform (4 – 75 ml. portions). The chloroform extracts were combined, washed with .2N NaOH, sat. aq. NaCl, dried ovr $Na_2SO_4$, filtered, and evaporated in vacuo to give a light foam of 0.80 g. (85%). This material was then reduced with $NaBH_4$ in methanol as per the procedure of Gates, et al. to codeine (.76 g.; 95%; 81% from neopinone); one peak by gc. coincident with the natural product and separable from neopine; m.p. 156° – 157° C. ($CH_3OH$).

This reaction was performed starting with 2.72 g. of neopinone to give 2.44 g. (90%) of codeinone which was reduced to codeine in 93% (2.28 g.; 83.5% from neopinone).

As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. A compound represented by the following formula:

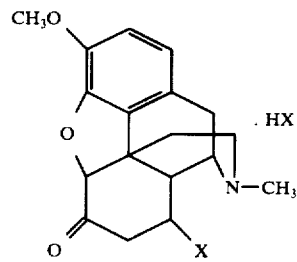

wherein X is a halogen selected from the group consisting of chlorine, bromine and iodine.

2. A compound according to claim 1 wherein X is chlorine.

3. A compound according to claim 1 wherein X is bromine.

4. A process for preparing codeinone which involves
   A. reacting neopinone or a mixture containing neopinone and codeinone with a hydrohalic acid selected from the group consisting of hydrochloric, hydrobromic and hydroiodic under anhydrous conditions to form the corresponding 8-halodihydrocodeinone hydrohalide,
   B. treating the 8-halodihydrocodeinone hydrochloride with a basic agent to form codeinone.

5. A process according to claim 4 wherein the acid is hydrochloric or hydrobromic.

6. A process according to claim 5 wherein the neopinone or the mixture is reacted with the hydrohalic acid in a suitable neutral non-protonic solvent solvent.

7. A process according to claim 6 wherein the solvent is methylene chloride, chloroform or ether.

8. A process according to claim 5 wherein the 8-halodihydrocodeinone hydrochloride is treated with a basic agent in an aqueous media.

9. A process according to claim 8 wherein the basic agent is sodium hydroxide, potassium hydroxide, ammonium hydroxide or an alkalimetal carbonate.

10. A process for preparing codeinone which involves
    A. reacting a solution of neopinone or a mixture containing neopinone and codeinone in methylene chloride with hydrobromic or hydrochloric acid in diethyl ether under anhydrous conditions at a temperature of from about 0° C. to about 30° C. to form the corresponding 8-halodihydrocodeinone hydrohalide, said hydrobromic or hydrochloric acid being present in an amount of from about 2 to 4 moles per mole of neopinone.

B. treating the 8-halodihydrocodeinone hydrochloride with sodium hydroxide so that the pH of the final mixture containing codeinone is from about 8 to 13.

11. A process for preparing 8-halodihydrocodeinone hydrohalide which comprises reacting neopinone or a mixture containing neopinone and codeinone with a hydrohalic acid selected from the group consisting of hydrochloric, hydrobromic and hydroiodic under anhydrous conditions to form the corresponding 8-halodihydrocodeinone hydrohalide.

12. A process according to claim 11 wherein the hydrohalic acid is hydrochloric or hydrobromic.

13. A process according to claim 12 wherein the neopinone or the mixture is reacted with the hydrochloric or hydrobromic acid in a suitable neutral non-protonic solvent.

14. A process according to claim 13 wherein the solvent is methylene chloride, chloroform or diethyl ether.

* * * * *